United States Patent
Miyamoto et al.

(10) Patent No.: US 6,840,930 B1
(45) Date of Patent: Jan. 11, 2005

(54) DISPOSABLE ABSORBENT ARTICLE HAVING REINFORCED EAR PANELS

(75) Inventors: Kouichi Miyamoto, Kobe (JP); Yukio Heki, Kobe (JP); Masataka Sugita, Suita (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/647,833

(22) PCT Filed: Apr. 23, 1998

(86) PCT No.: PCT/US98/08205

§ 371 (c)(1),
(2), (4) Date: Oct. 5, 2000

(87) PCT Pub. No.: WO99/53878

PCT Pub. Date: Oct. 28, 1999

(51) Int. Cl.[7] ................................................ A61F 13/15
(52) U.S. Cl. ............................ 604/385.31; 604/385.03; 604/385.04; 604/385.28
(58) Field of Search ...................... 604/385.28, 385.26, 604/385.04, 385.03, 385.01, 385.31

(56) References Cited

U.S. PATENT DOCUMENTS

| | | | | |
|---|---|---|---|---|
| 4,808,177 A | * | 2/1989 | DesMarais et al. | 604/385.27 |
| 5,246,432 A | * | 9/1993 | Suzuki et al. | 604/385.25 |
| 5,346,486 A | * | 9/1994 | Osborn et al. | 604/385.04 |
| 5,346,487 A | | 9/1994 | Lovestedt | |
| 5,593,401 A | * | 1/1997 | Sosalla et al. | 604/385.2 |
| 5,620,431 A | * | 4/1997 | LeMahieu et al. | 604/385.25 |
| 5,624,424 A | * | 4/1997 | Saisaka et al. | 604/385.2 |
| 5,628,738 A | * | 5/1997 | Suekane | 604/385.1 |
| 5,674,215 A | | 10/1997 | Ronnberg | |
| 5,730,738 A | * | 3/1998 | McFall et al. | 604/387 |
| 6,120,488 A | * | 9/2000 | Van Rijswijck et al. | 604/385.2 |
| 6,123,694 A | * | 9/2000 | Pieniak et al. | 604/385.2 |

FOREIGN PATENT DOCUMENTS

| | | |
|---|---|---|
| EP | 0 403 832 A | 12/1990 |
| EP | 0 409 149 A | 1/1991 |
| GB | 2 278 993 A | 12/1994 |
| JP | 3009482 B2 | 2/2000 |
| JP | 3134567 B2 | 2/2001 |
| WO | WO 97/30671 A2 | 8/1997 |
| WO | WO 97 30671 | 8/1997 |

\* cited by examiner

Primary Examiner—Jacqueline Stephens
(74) Attorney, Agent, or Firm—Jack L Oney, Jr.; Jay A. Krebs; Ken K. Patel (57) ABSTRACT

Disclosed is an absorbent article having a longitudinal centerline and a lateral centerline, comprising; (a) a containment assembly having a rear waist region, a crotch region, a front waist region, a pair of longitudinal edges, a body facing surface and a garment facing surface opposite to the body facing surface, the containment assembly comprising a topsheet, a backsheet joined to the topsheet, an absorbent core positioned between the topsheet and the backsheet, and a pair of barrier leg cuffs having a proximal edge and a distal edge and being positioned adjacent to the longitudinal edges of the containment assembly; (b) a pair of rear ear panels extending laterally outwardly from the proximal edges of the barrier leg cuff in the rear waist region; (c) a pair of front ear panels extending laterally outwardly from the proximal edges of the barrier leg cuff in the front waist region; and (d) a reinforcement nonwoven joined to at least one of either the rear ear panels or the front ear panels, the reinforcement nonwoven not substantially overlapping the containment assembly.

11 Claims, 5 Drawing Sheets

DISPOSABLE ABSORBENT ARTICLE HAVING REINFORCED EAR PANELS

FIELD

The present invention relates to disposable absorbent articles, and more particularly to disposable absorbent articles having reinforced ear panels.

BACKGROUND

Infants and other incontinent individuals wear absorbent articles such as diapers to receive and contain urine and other body exudates. Absorbent articles function both to contain discharged materials and to isolate the materials from the body of the wearer and from the wearer's garments and bed clothing. Disposable absorbent articles having many different basic designs are known in the art, including tape type diapers in which the rear portion of the diaper is attached to the front portion of the diaper on each side of the wearer, and "pull-on" type diapers which allow the wearer to pull the absorbent article on as pants and which do not require any of the fastening steps of the tape type designs.

It is also known that the exterior of disposable diapers can be covered with a flexible, liquid and vapor impervious sheet to prevent any absorbed liquid from passing through the diaper and soiling adjacent articles such as clothing, bedding and the like. These outer covers, generally referred to as backsheets, are often constructed from fluid impervious films such as polyethylene. Although such backsheets do prevent liquid from passing through the diaper, they also can make the diaper feel hot and uncomfortable to wear because of their impermeability to air and/or moisture, particularly in the back waist and side ear regions of the article.

Some disposable diapers are provided with a nonwoven material laminated or otherwise adhered to the backsheet film to provide the appearance of cloth and a cloth-like feel on the outside of the garment such that wearers and caregivers perceive a garment-like feel. However,such garments can be stiff, bulky or rough on the surface. The use of such nonwoven materials may also increase the raw material costs associated with production of the absorbent articles, especially for larger-sized garments, for example, as used by incontinent or bedridden adults.

Thus, there remains a desire to provide disposable absorbent articles with breathability and softness, particularly in the side ear area, without compromising strength and while still being cost-effective to produce. None of the existing art provides all of the advantages and benefits of the present invention.

SUMMARY

The present invention is directed to an absorbent article having a longitudinal center line and a lateral centerline, comprising; (a) a containment assembly having a rear waist region, a crotch region, a front waist region, a pair of longitudinal edges, a body facing surface and a garment facing surface opposite to the body facing surface, the containment assembly comprising a topsheet, a backsheet joined to the topsheet, an absorbent core positioned between the topsheet and the backsheet, and a pair of barrier leg cuffs having a proximal edge and a distal edge and being positioned adjacent to the longitudinal edges of the containment assembly; (b) a pair of rear ear panels extending laterally outwardly from the proximal edges of the barrier leg cuff in the rear waist region; (c) a pair of front ear panels extending laterally outwardly from the proximal edges of the barrier leg cuff in the front waist region; and (d) a reinforcement nonwoven joined to at least one of either the rear ear panels or the front ear panels, the reinforcement nonwoven not substantially overlapping the containment assembly.

These and other features, aspects, and advantages of the present invention will become evident to those skilled in the art from a reading of the present disclosure.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION

The present invention relates to disposable absorbent articles. As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

Figure 1:
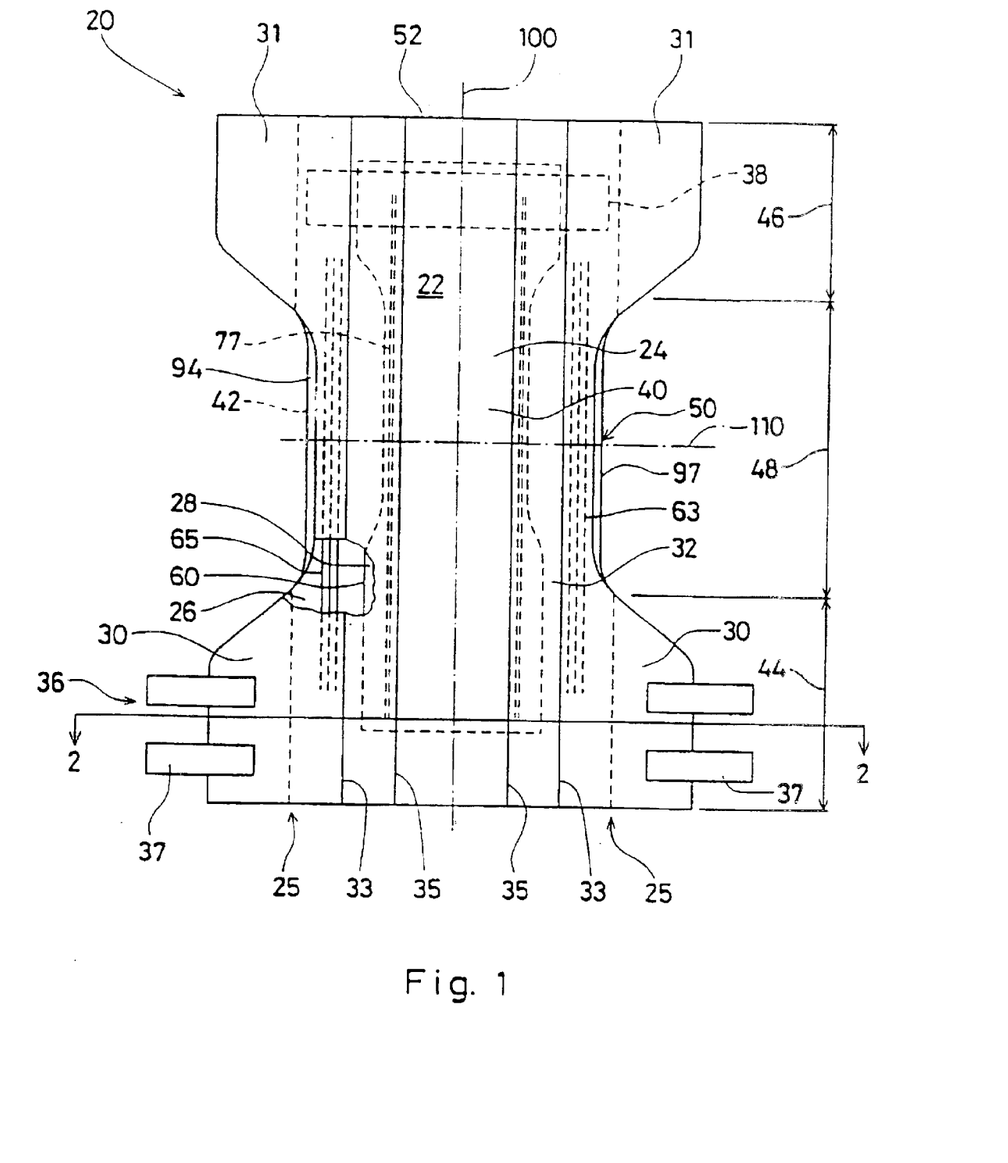
FIG. 1 is a plan view of a preferred embodiment of the present invention having portions cut away to reveal underlying structure, with the inner (body facing) surface of the article facing the viewer.

A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

FIG. 1 is a plan view of the diaper 20 in its flat-out, uncontracted state (i.e., with elastic-induced contraction pulled out) with portions of the structure being cut-away to more clearly show the construction of the diaper 20 and with the portion of the diaper 20 which faces the wearer, the inner surface (i.e., body facing surface) 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges 60. The backsheet 26 prevents the exudates absorbed and contained in the absorbent core 28 from wetting articles which contact the diaper 20 such as bed sheets and undergarments. The diaper preferably further comprises front ear panels 31; rear ear panels 30; barrier leg cuffs 32; and a fastening system 36 preferably comprising at least one pair of securement members 37 and a landing member 38. Waist elastic (not shown) may further be provided.

The diaper 20 has an inner surface 40 (facing the viewer in FIG. 1), an outer surface (i.e., garment facing surface) 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the side edges are designated 50 and the end edges are designated 52. The rear waist region 44 and the front waist region 46 extend from the end edges 52 of the periphery to the crotch region 48.

The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The term "transverse", as used herein, refers to a line, axis or direction which lies within the plane of the diaper that is generally perpendicular to the longitudinal direction (which divides the wearer into front and back body halves).

The topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" issued to Kenneth B. Buell et al., on Sep. 29, 1992.

Elastically contractible gasketing cuffs 63 are disposed adjacent the periphery of the diaper 20, preferably adjacent to each barrier leg cuff 32 along each side edge 50, so that the gasketing cuffs 63 tend to draw and hold the diaper 20 against the legs of the wearer. Alternatively, a gasketing cuff 63 may be disposed adjacent either or both of the end edges 52 to provide a waistcuff. The gasketing cuffs may comprise any means as are well known in the diaper art, see, e.g., Buell U.S. Pat. No. 3,860,003 and Kievet et al. U.S. Pat. No. 4,515,595. In a preferred embodiment as shown in FIG. 1, the gasketing cuff 63 is formed form the extension of the backsheet 26 and a portion of the barrier leg cuff 32 extending outwardly from and along the longitudinal edges 60 of the absorbent core 28 in at least the crotch region 48.

Flap elastic members 65 are operatively associated with the gasketing cuffs 63 in an elastically contractible condition so that in a normally unrestrained configuration, the flap elastic members effectively contract or gather the gasketing cuffs. The length of the flap elastic members 65 is generally dictated by the diaper's design and may be affixed to the diaper by any means known in the art.

The absorbent core 28 may be any absorbent member which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the front waist region but a generally rectangular shape in the rear waist region. Other exemplary absorbent structures for use as the absorbent core 28 of the present invention are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

The absorbent core 28 may alternatively comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992.

The topsheet 24 is preferably joined to the absorbent core 28 and to the backsheet 26 by attachment means (not shown) such as those well known in the art. In a preferred embodiment of the present invention, the topsheet 24 and the backsheet 26 are joined directly to each other in the diaper periphery and are indirectly joined together by directly joining them to the absorbent core 28 by any suitable attachment means known to those of skill in the art.

The topsheet 24 is preferably compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is preferably treated to be hydrophilic so that liquids will transfer through the topsheet more rapidly. This diminishes the likelihood that body exudates will flow off the topsheet 24 rather than being drawn through the topsheet 24 and being absorbed by the absorbent core 28.

The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991.

An alternative preferred topsheet 24 comprises an apertured formed film. Apertured formed films are useful for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr et al. on Jul. 31, 1984; and U.S. Pat. No. 5,006,394 "Multilayer Polymeric Film" issued to Baird on Apr. 9,1991.

The diaper 20 preferably further comprises elasticized barrier leg cuffs 32 positioned adjacent to the longitudinal edges 25 of the containment assembly. The barrier leg cuffs 32 provide improved containment of liquids and other body exudates. Each barrier leg cuff 32 may comprise any of several different embodiments for reducing the leakage of body exudates in the leg regions. (The barrier leg cuff 32 is sometimes also referred to as leg bands, side flaps, elasticized leg cuffs, or elastic cuffs.) Non-limiting examples of embodiments for barrier leg cuffs herein are described in the following U.S. patents. U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,795,454 entitled "Absorbent Article Having Leakage Resistant Dual Cuffs issued to Dragoo on Jan. 3, 1989 describes leakage resistant cuffs. U.S. Pat. No. 4,704,115 entitled "Disposable Waste Containment Garment" issued to Buell on Nov. 3, 1987, discloses a disposable diaper or incontinence garment having side-edge-leakage-guard gutters configured to contain free liquids within the garment.

Each barrier leg cuff 32 has a proximal edge 33 joined with the containment assembly 22, a distal edge 35, and a spacing means 77 such as a spacing elastic member 77 for spacing the distal edge 35 away from the liquid receiving surface (topsheet 24) of the containment assembly 22. The proximal edge 33 of the barrier leg cuff 32 is preferably inboard of the gasketing cuff 63, preferably between the longitudinal edge 60 of the core 28 and the flap elastic members 65 by adjoining a segment of the barrier leg cuff to the backsheet 26 by a seal means (not separately shown) such as an adhesive bead so as to form a leakage resistant seal along the proximal edge 33 to present a barrier to liquid wicking through the topsheet 24 so as to prevent the liquids from wicking underneath the barrier cuffs 32 to the edges of the diaper 20.

Figure 2A:
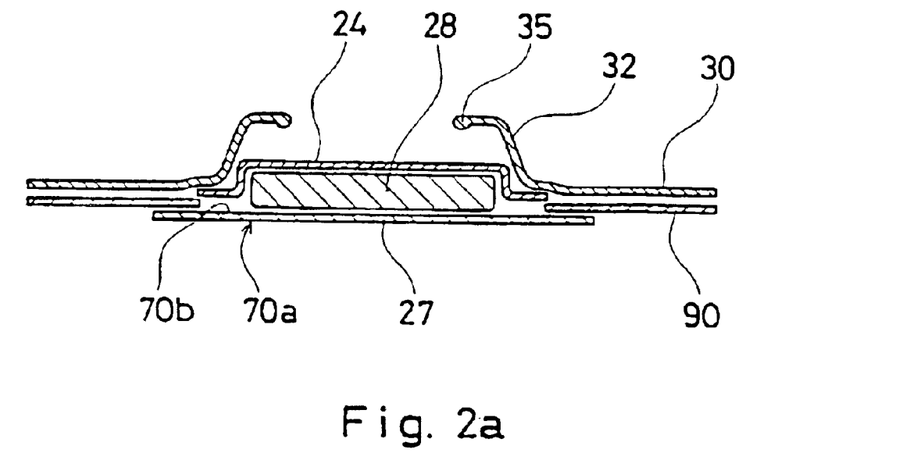
FIG. 2a is a simplified cross sectional view taken along the section line 2—2 of FIG. 1.

The backsheet 26 of the present invention preferably comprises a plastic film 27 having an outer-facing surface 70a and a body-facing surface 70b, as shown in FIG. 2. The plastic film 27 is preferably impervious to liquids (e.g., urine) and is preferably manufactured from a thin plastic film. However, the plastic film 27 preferably permits vapors to escape from the diaper 20. In a preferred embodiment, a microporous polyethylene film is used for the plastic film. A suitable microporous polyethylene film is manufactured by Mitsui Toatsu Chemicals, Inc., Nagoya, Japan and marketed in the trade as Espoir.

A suitable material for the plastic film is a thermoplastic film having a thickness of from about 0.012 mm (0.5 mil) to about 0.051 mm (2.0 mils), preferably comprising polyethylene or polypropylene. Preferably, the plastic film has a basis weight of from about 5 $g/m^2$ to about 35 $g/m^2$. However, it should be noted that other flexible liquid impervious materials may be used. As used herein, the term "flexible" refers to materials which are compliant and which will readily conform to the general shape and contours of the wearer's body.

In conventional diapers (not shown), the backsheet 26 typically comprises a plastic film 27 and a nonwoven web joined with the outer-facing surface 70a of the plastic film 27 to form a laminate. The nonwoven web typically covers all or substantially all of the outer-facing surface 70a of the plastic film 27 and extends over all of the containment assembly area 22, in the front waist region 46, the rear waist region 44, and the crotch region 48. In other words, the nonwoven web portion of this conventional backsheet laminate typically covers the entirety of the outer facing surface 42 of the diaper 20. This conventional configuration, while providing a certain degree of cloth-like feel and garment-like appearance, can be expensive due to the cost of the nonwoven laminate material itself as well as the manufacturing and/or supply costs of the lamination process, particularly for articles intended for adult use, due to the size of the articles. This may also feel stiff and uncomfortable for some wearers, particularly adult wearers.

Figure 3:
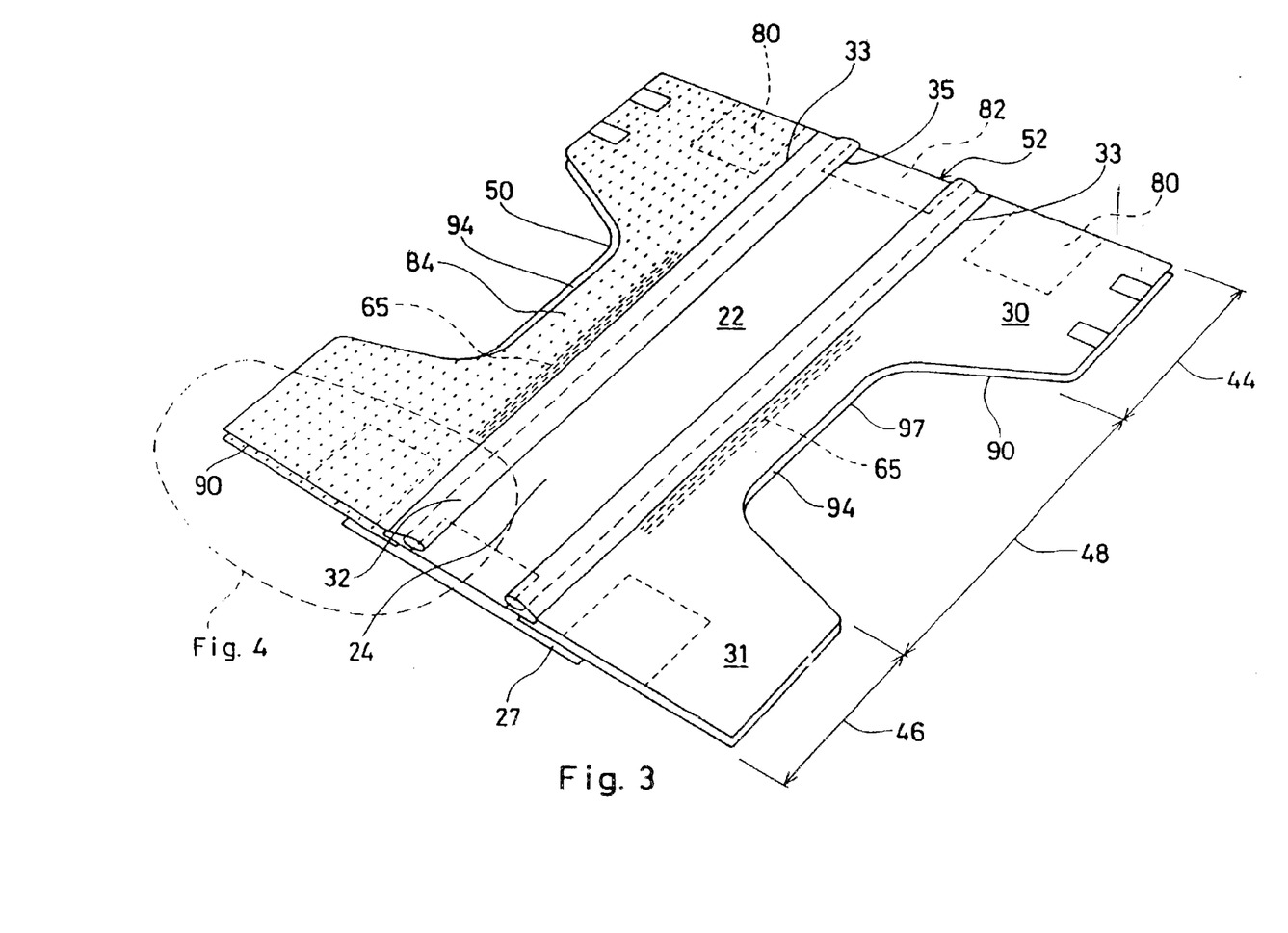
FIG. 3 is a perspective view of the embodiment shown in FIG. 1.
Figure 4:
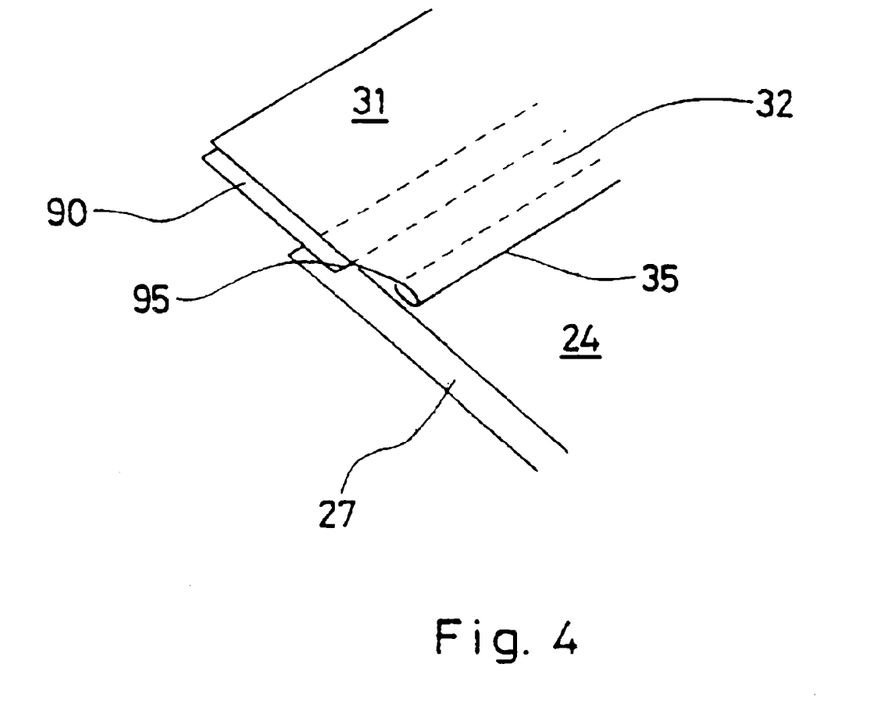
FIG. 4 is an enlarged view of a portion of FIG. 3.
Figure 5:
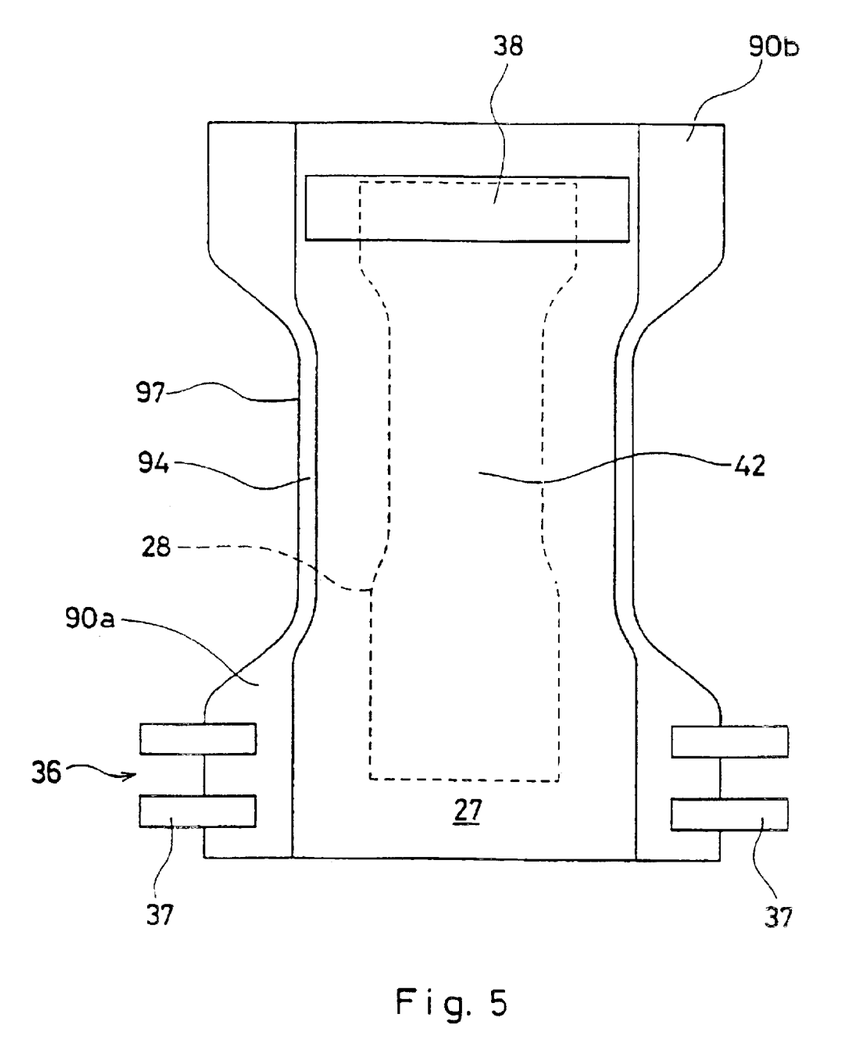
FIG. 5 is plan view of the embodiment shown in FIG. 1, with the outer (garment facing) surface of the article facing the viewer.

In preferred embodiments of the present invention, the conventional backsheet laminate comprised of a plastic polymer film and a nonwoven web that covers substantially all of the outer-facing surface 42 of the diaper is eliminated. Instead, a reinforcement nonwoven 90 that does not substantially overlap the containment assembly 22 is provided. Referring to FIGS. 3–5, in preferred embodiments of the present invention, the backsheet comprises a plastic film 27 existing in the containment assembly area 22. The plastic film 27 is not provided in the front and rear ear panel areas 30 and 31, since the plastic film 27 is not needed where there is no core material 28 to absorb exudates, particularly urine. The backsheet further comprises a nonwoven web; as noted above, this nonwoven 90 does not substantially overlap the containment assembly 22.

However, the elimination of the conventional layer of nonwoven material generally will have the disadvantage of reduction in the overall strength of the diaper in the ear regions. Therefore, in preferred embodiments of the present invention, a reinforcement nonwoven material 90 is provided in at least one of either the rear or front ear panel regions 30 or 31. Thus, the combination of the reinforcement nonwoven 90 and the nonwoven material of the ear panels 30 and/or 31, provides a strong and soft ear. In addition, bulkiness in the containment region 22 tends to be eliminated in such preferred embodiments since there is less material provided there. Such an elimination of bulk in the containment region 22 is particularly desirable in absorbent articles for adult wearers, since those articles tend to require a thicker core than might be needed for baby or child use.

In preferred embodiments of the present invention, the reinforcement nonwoven 90 can be provided in either of the rear ear panel regions 30 or the front ear panel regions 31. In other more preferred embodiments, the reinforcement nonwoven 90 can be provided in both of the rear and the front ear panel regions 30, 31.

With reference to FIGS. 3–5, a preferred configuration of the ear panels 30 and 31 will be described. Each of the rear ear panels 30 extends laterally outwardly from the proximal edges 33 of the barrier leg cuff 32 in the rear waist region 44. Each rear ear panel 30 preferably comprises an extension of the barrier leg cuff 32; preferably the rear ear panels 30 and the barrier leg cuff 32 formed from a continuous and unitary piece of material. Alternatively, multiple pieces of material may be provided, and these may be of the same or of differing materials.

Similarly, each of the front ear panels 31 extends laterally outwardly from the proximal edges 33 of the barrier leg cuff 32 in the front waist region 46. Each front ear panel 31 preferably also comprises an extension of the barrier leg cuff 32; preferably the front ear panels 31 and the barrier leg cuff 32 formed from a continuous and unitary piece of material. Alternatively, multiple pieces of material may be provided, and these may be of the same or of differing materials.

Highly preferable is the configuration in which all of the rear ear panel 30, the front ear panel 31, and the barrier leg cuff 32 are formed from a continuous and unitary piece of material, preferably a nonwoven material.

The reinforcement nonwoven 90 is preferably joined to at least one of either the rear ear panels 30 or the front ear panels 31. Preferably, the reinforcement nonwoven 90 is positioned relative to the barrier leg cuff 32 such that the reinforcement nonwoven 90 is a part of the outer facing surface 42 of the diaper 20 and the rear ear panel 30 is part of the inner facing surface 40 of the diaper. The proximal edge 95 of the reinforcement nonwoven 90 is preferably secured between the backsheet plastic film 27 and the barrier leg cuff 32. This preferred arrangement is shown in FIG. 3 and can be more clearly seen in the enlarged portion shown in FIG. 4.

Preferably, the ear panel 30 and/or 31 is secured to the reinforcement nonwoven 90 located in that ear region by a continuous bead glue over the entire juxtaposed area. This means of securing the two nonwoven layers is believed to provide good strength and integrity without causing stiffness. Alternatively, any other means of attachment known to those of skill in the art may be used to secure the two nonwovens that comprise the ear panel and the reinforcement nonwoven.

The reinforcement nonwoven 90 is provided so as not to substantially overlap the containment assembly 22. For example, as can be most clearly seen in FIG. 5, which is an view of the outer (garment) facing surface of the absorbent article, substantially no reinforcement nonwoven 90 material is provided in the containment assembly region 22.

In preferred embodiments in which the rear ear panels 30 are provided with the reinforcement nonwoven 90a and the front ear panels 31 are also provided with the reinforcement nonwoven 90b, it is preferred that the reinforcement nonwoven 90 further comprises a strip 94 of nonwoven material extending longitudinally in the crotch region. This preferred configuration for the reinforcement nonwoven is clearly shown in FIG. 5. More preferably, the reinforcement nonwoven 90 and the strip 94 are cut from a single piece of material to form a continuous piece of nonwoven material, as shown in FIG. 5.

However, the reinforcement nonwoven 90 may alternatively be provided in any or all of the front, crotch, and rear regions of the diaper. It may be provided as a unitary piece of nonwoven material, which is preferred as described above, or may alternatively be provided in discrete segments. if provided in discrete segments, each segment may be of the same or of a different material composition.

In preferred embodiments, the strip region 94 of the reinforcement nonwoven 90, which is located in the crotch region 48, has a distal edge 97 that extends more distally outward from the longitudinal centerline 100 than does the proximal edge 33 of the barrier leg cuff 32. Thus, the distal edge 97 of the strip 94 forms a part of the side edge 50 of the periphery of the diaper. This construction provides increased wearer comfort as follows. A portion of the plastic film 27 of the backsheet is laminated to the barrier leg cuff 32 in order to prevent leakage. This plastic 27 is a part of the outer facing surface 42 of the diaper, and it tends to contact the wearer's body in the leg area of the wearer's crotch region. Typically, this is stiff and can cause a "stuffy" feeling or other discomfort for the wearer. However, by extending the distal edge 97 of the strip 94 beyond the proximal edge 33 of the barrier leg cuff 32 such that the strip 94 is made a part of the side edge 50 (i.e., the periphery) of the diaper, as shown in FIGS. 1, 3, and 5, the comparatively softer nonwoven material of the strip 94 comes into contact with the wearer's skin, rather than the comparatively stiffer plastic material 27 of the backsheet.

In preferred embodiments as shown most clearly in FIG. 4, the reinforcement nonwoven 90 is secured to the containment assembly 22 between the plastic film 27 and the barrier leg cuff 32. As shown in FIG. 3, the reinforcement nonwoven 90 may be secured to the containment assembly 22 by the chassis bead glue 84 and the side seal glue 80. Such glues are typically used to secure the components of disposable absorbent articles. (For ease of illustration, the chassis bead glue 84 is shown on one side of the diaper only.)

In the typical constructions of absorbent articles having side seal glue 80, it is common for the side seal glue 80 to be completely cut out in the crotch region 48 during the manufacturing process, in which the leg openings formed in the crotch region 48 are cut out after the various components of comprising the diaper 20 are combined. Thus, if the typical construction were to be used in connection with preferred embodiments of the present invention, the strip 94 of reinforcement nonwoven 90 would be left completely or mostly unattached to the remainder of the article in the crotch region 48. This is undesirable, for not only would the risk of leakage increase, but also such an unattached strip could easily be torn. In addition, a generally unattractive appearance, inconvenience is application during caregiving, and discomfort during wear would likely result.

In preferred embodiments of the present invention, this problem is solved by providing the strip 94 with sufficient width in the crotch region 48 such that the chassis bead glue 84 that is applied between the leg elastics 65 and the side edge 50 also secures the strip 94 to the containment assembly 22.

Thus, in preferred embodiments of the present invention as described above, the strip 94 is securely attached over its entire length and width to the containment assembly. In addition, securing the strip 94 by means of the chassis bead glue 84 is preferred. The chassis bead glue application provides a soft, comfortable feel for the wearer due to the flexible open areas between the beads, while also providing bond integrity and strength. Alternatively, other means of securing the strip 94 to the containment assembly 22 that are known to those of sill in the art may be used.

As in conventional articles, end seal glue 82 is also provided, shown as shaded regions in FIG. 3, in the front waist and rear waist regions 44 and 46. This end seal glue 82 serves to prevent leakage from the front and rear waist regions 44 and 46, since the core 28 typically does not extend all the way to the end edges 52 of the periphery of the article.

In addition, attaching the reinforcement nonwoven 90 and the strip 94 in the preferred manner described herein also helps to avoid skin irritation for the wearer, because no seam that comes into contact with the wearer's skin is created.

Alternatively, the proximal edge 95 of the reinforcement nonwoven 90 may be secured to the outer facing surface plastic film 27; however, in such an embodiment, bonding of the strip 94 to the containment assembly 22 tends to be made more difficult.

Preferably the nonwoven material used for the barrier leg cuff 32 and the nonwoven material used for the reinforcement nonwoven have substantially the same modulus. Thus the two materials experience approximately the same recoverability during and after stretch. This contributes to better fit and better comfort for the wearer and greater ease of application.

Figure 2B:
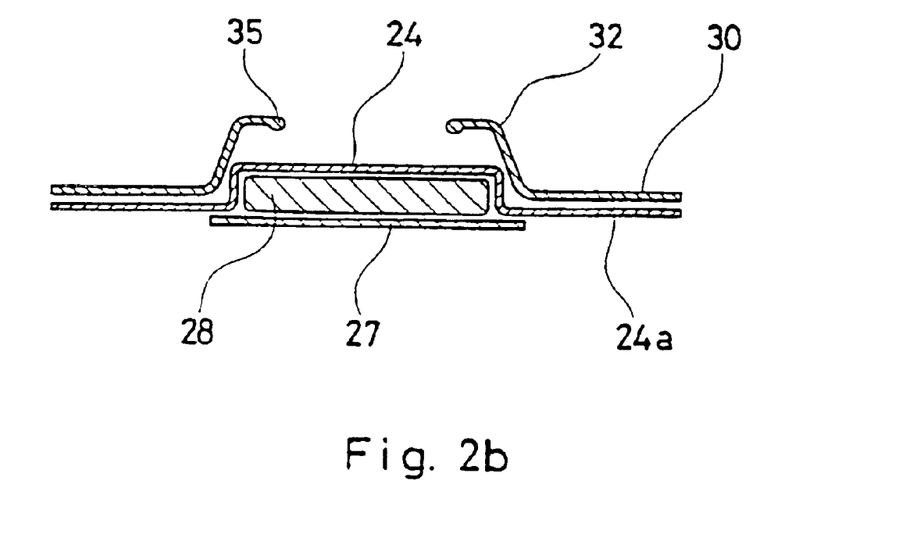
FIG. 2b is a simplified cross sectional view of another embodiment of the present invention taken along the section line 2—2 of FIG. 1.

In an alternative embodiment shown in FIG. 2b, the topsheet 24 may be extended to be adjacently juxtaposed with the barrier leg cuff 32 and the rear ear panel 30 (and/or the front ear panel 31). In this embodiment the extension 24a of the topsheet 24 serves essentially the same function as the reinforcement nonwoven. The extension 24a of the topsheet may be provided in any or all of the rear ear panel, the front ear panel or the crotch region. However, there may be an increased risk of leakage associated with this embodiment, as the hydrophilicity of at least some portions of the topsheet material may contribute to wicking of liquid. For example, to alleviate risk of leakage in such embodiments, the topsheet 24 could be made hydrophilic in the core area, and treated to be rendered hydrophobic in the extension areas 24a. However, the costs associated with such a treatment of the topsheet tend to be increased.

The nonwoven web materials useful for the ear panels, barrier leg cuffs, and the reinforcement nonwoven are preferably air pervious. The nonwoven web may comprise natural fibers (e.g. cotton or wood fibers), or may comprise fibers of polyethylene, polypropylene, polyester, polyethylene terephthalate, or any combination of such fibers. Further, the nonwoven web may be carded, spunmelt, meltblown or air-through bonded or have any other characteristic or be manufactured in any manner known in the art. Preferably, the nonwoven web is comprised of sufficient thermoplastic material to allow for thermal bonding of the material to other components of the diaper.

A nonwoven web suitable for use herein is a spunbonded nonwoven web, preferably made of bi-component fibers. Preferably, the bi-component fiber contains a polyethylene and a polypropylene. More preferably, the bi-component fiber has a core of the polypropylene and a sheath of the polyethylene. The bi-component fiber preferably has from about 55% to about 95% by weight of the polyethylene. Most preferably, the bi-component fiber has from about 70% to about 90% by weight of the polyethylene.

The spunbonded nonwoven web is desirably placed in the disposable absorbent article so that the fiber direction of the spunbonded bi-component plastic fibers is aligned with the longitudinal direction of the disposable absorbent article. Preferably, the spunbonded nonwoven web has a tensile strength of at least 80 gf/cm, more preferably of at least 180 gf/cm in the traverse direction of the disposable absorbent article.

Another suitable nonwoven web is a carded nonwoven web, preferably made of bi-component fibers. Preferably, the bi-component fiber contains a polyethylene and a polyethylene terephthalate. Preferably, the bi-component fiber has a core of the polyethylene terephthalate and a sheath of the polyethylene. In preferred embodiments, the bi-component fiber has from about 50% to about 95% by weight of the polyethylene. Most preferably, the bi-component fiber has from about 55% to about 95% by weight of the polyethylene.

In a further alternative embodiment, the bi-component fiber may contain different types of polypropylene. More preferably, the bi-component fiber has a core of the polypropylene which has a higher melting point and a sheath of the polyethylene which has a lower melting point.

In a preferred embodiment, the nonwoven web is a carded nonwoven web obtainable from Havix Co., LTD., Gifu, Japan as E-2341. The nonwoven web is made of bi-component fibers of a polyethylene (PE) and a polyethylene terephthalate (PET). The ratio of PE/PET is about 60/40. The PE/PET bi-component fiber has the dimension of 2d×51 mm.

In an alternative preferred embodiment, the nonwoven web is a spunbonded nonwoven web obtainable from Mitsui Petrochemical Industries, Ltd., Tokyo, Japan. The nonwoven web is made of bi-component fibers of a polyethylene (PE) and a polypropylene (PP). The ratio of PE/PP is about 80/20. The PEIPP bi-component fiber has the thickness is approximately 2.3d.

The backsheet 26 is preferably positioned adjacent the outer surface of the absorbent core 28 and is preferably joined thereto by any suitable attachment means known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

Embodiments of the present invention are also contemplated wherein the absorbent core is not joined to the backsheet 26, and/or the topsheet 24 in order to provide greater extensibility in the front waist region 46 and the rear waist region 44. Alternative embodiments are contemplated wherein an additional member, such as a liquid impervious barrier material(s) (not shown), is positioned between the outer facing surface of the absorbent core 28 and the backsheet 26. Any such barrier member may or may not be joined to the absorbent core 28. Further, the backsheet 26 may or may not be joined to any barrier material(s) that are positioned between the backsheet 26 and the absorbent core 28.

The embodiments disclosed herein have many advantages. For example, they can provide better breathability and softness in the ear regions of the absorbent article without compromising the strength of the article in the these regions, and can further provide cost savings, since the quantity of nonwoven material needed per article is reduced. Wearer comfort is also believed to be increased with the embodiments of the present invention disclosed herein.

All cited references are incorporated herein by reference in their entireties. Citation of any reference is not an admission regarding any determination as to its availability as prior art to the claimed invention.

It is understood that the examples and embodiments described herein are for illustrative purposes only and that various modifications or changes in light thereof will be suggested to one skilled in the art without departing from the scope of the present invention.

What is claimed is:

1. An absorbent article having a longitudinal centerline and a lateral centerline, an inner surface and a garment facing surface, the absorbent article comprising:

a containment assembly having a rear waist region, a crotch region, a front waist region, a pair of longitudinal edges, a body facing surface and a garment facing surface opposite to the body facing surface, the containment assembly comprising a topsheet, a backsheet joined to the topsheet, an absorbent core positioned between the topsheet and the backsheet, and a pair of barrier leg cuffs having a proximal edge and a distal edge and being positioned adjacent to the longitudinal edges of the containment assembly;

a pair of rear ear panels extending laterally outwardly from the proximal edges of the barrier leg cuff in the rear waist region;

a pair of front ear panels extending laterally outwardly from the proximal edges of the barrier leg cuff in the front waist region; and a reinforcement nonwoven disposed between the backsheet and a barrier leg cuff and joined to an inner-facing surface of the backsheet and to at least one of either the garment facing surface of the rear ear panels or the garment facing surface of the front ear panels so as to form a portion of the garment facing surface of the absorbent article, the reinforcement nonwoven not substantially overlapping the containment assembly wherein the reinforcement nonwoven does not extend the entire longitudinal length of the absorbent article.

2. The absorbent article of claim 1 wherein the rear ear panels comprise extensions of the barrier leg cuffs in the rear waist region.

3. The article of claim 2 wherein the front ear panels comprise extensions of the barrier leg cuff in the front waist region.

4. The absorbent article of claim 3 wherein the reinforcement nonwoven is joined to both the rear ear panels and the front ear panels.

5. An absorbent article having a longitudinal center line and a lateral centerline, an inner surface and a garment facing surface, comprising:

a containment assembly having a rear waist region, a crotch region, a front waist region, a pair of longitudinal edges, a body facing surface and a garment facing surface opposite to the body facing surface, the containment assembly comprising a topsheet, a backsheet joined to the topsheet, an absorbent core positioned between the topsheet and the backsheet, and a pair of barrier leg cuffs having a proximal edge and a distal edge and being positioned adjacent to the longitudinal edges of the containment assembly;

a pair of rear ear panels extending laterally outwardly from the proximal edges of the barrier leg cuff in the rear waist region;

a pair of front ear panels extending laterally outwardly form the proximal edges of the barrier leg cuff in the front waist region; and a reinforcement nonwoven joined to an inner-facing surface of the backsheet and to at least one of either the garment facing surface of the rear ear panels or the garment facing surface of the front ear panels so as to form a portion of the garment facing surface of the absorbent article, the reinforcement nonwoven not substantially overlapping the containment assembly, the reinforcement nonwoven having a tensile strength of at least 80 gf/cm in the traverse direction of the absorbent article.

6. An absorbent article having a longitudinal centerline and a lateral centerline, an inner surface and a garment facing surface, the absorbent article comprising:

a containment assembly having a rear waist region, a crotch region, a front waist region, a pair of longitudinal edges, a body facing surface and a garment facing surface opposite to the body facing surface, the containment assembly comprising a topsheet, a backsheet joined to the topsheet, an absorbent core positioned between the topsheet and the backsheet, and a pair of barrier leg cuffs having a proximal edge and a distal edge and being positioned adjacent to the longitudinal edges of the containment assembly;

a pair of rear ear panels extending laterally outwardly from the proximal edges of the barrier leg cuff in the rear waist region;

a pair of front ear panels extending laterally outwardly from the proximal edges of the barrier leg cuff in the front waist region; and a reinforcement nonwoven joined to an inner-facing surface of the backsheet and to at least one of either the garment facing surface of the rear ear panels or the garment facing surface of the front ear panels so as to form a portion of the garment facing surface of the absorbent article, the reinforcement nonwoven not substantially overlapping the containment assembly wherein the reinforcement nonwoven does not extend the entire longitudinal length of the absorbent article and wherein the reinforcement nonwoven further comprises a strip which is joined to the longitudinal edges of the containment assembly in the crotch region.

7. The absorbent article of claim 6 wherein the reinforcement nonwoven and the strip are a continuous piece of material.

8. The absorbent article of claim 7 wherein the reinforcement nonwoven has a proximal edge, the proximal edge of the reinforcement nonwoven being joined to the barrier leg cuff between the backsheet and the barrier leg cuff.

9. The absorbent article of claim 8 wherein the strip has a distal edge that extends more distally outward from the longitudinal centerline than the proximal edge of the barrier leg cuff.

10. The absorbent article of claim 9 wherein both of the barrier leg cuffs and the reinforcement nonwoven comprise a hydrophobic nonwoven material.

11. An absorbent article having a longitudinal center line and a lateral centerline, an inner surface and a garment facing surface, the absorbent article comprising:

a containment assembly having a rear waist region, a crotch region, a front waist region, a pair of longitudinal edges, a body facing surface and a garment facing surface opposite to the body facing surface, the containment assembly comprising a topsheet, a backsheet joined to the topsheet, an absorbent core positioned between the topsheet and the backsheet, and a pair of barrier leg cuffs having a proximal edge and a distal edge and being positioned adjacent to the longitudinal edges of the containment assembly;

a pair of rear ear panels extending laterally outwardly from the proximal edges of the barrier leg cuff in the rear waist region;

a pair of front ear panels extending laterally outwardly form the proximal edges of the barrier leg cuff in the front waist region; and a reinforcement nonwoven disposed between the backsheet and a barrier leg cuff and joined to an inner-facing surface of the backsheet and to at least one of either the garment facing surface of the rear ear panels or the garment facing surface of the front ear panel so as to form a portion of the garment facing surface of the absorbent article, wherein the reinforcement nonwoven does substantially overlap the containment assembly, whereby the reinforcement nonwoven provides topsheet-like benefits.

* * * * *

UNITED STATES PATENT AND TRADEMARK OFFICE
CERTIFICATE OF CORRECTION

PATENT NO. : 6,840,930 B1
DATED : January 11, 2005
INVENTOR(S) : Miyamoto et al.

It is certified that error appears in the above-identified patent and that said Letters Patent is hereby corrected as shown below:

Title page,
Item [75], Inventors, delete "Suita" and insert -- Osaka --.

Column 1,
Line 40, delete "However,such" and insert -- However, such --.

Column 3,
Line 47, delete "worm" and insert -- worn --.

Column 11,
Line 13, delete "PEIPP" and insert -- PE/PP --.

Column 12,
Line 43, delete "center line" and insert -- centerline --.
Line 45, after "surface," and insert -- the absorbent article".
Line 60, delete "form" and insert -- from --.

Column 14,
Line 10, delete "center line" and insert -- centerline --.
Line 27, delete "form" and insert -- from --.

Signed and Sealed this

Twenty-first Day of February, 2006

JON W. DUDAS
*Director of the United States Patent and Trademark Office*